US008993617B2

(12) United States Patent
Koong et al.

(10) Patent No.: US 8,993,617 B2
(45) Date of Patent: Mar. 31, 2015

(54) IRE1ALPHA ENDONUCLEASE SPECIFIC INHIBITOR WITH CYTOTOXIC ACTIVITY

(75) Inventors: Albert C. Koong, Los Altos, CA (US); Ioanna Papandreou, Columbus, OH (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 27 days.

(21) Appl. No.: 13/883,502

(22) PCT Filed: Nov. 8, 2011

(86) PCT No.: PCT/US2011/059821
§ 371 (c)(1),
(2), (4) Date: Jul. 25, 2013

(87) PCT Pub. No.: WO2012/064774
PCT Pub. Date: May 18, 2012

(65) Prior Publication Data
US 2013/0303599 A1    Nov. 14, 2013

Related U.S. Application Data

(60) Provisional application No. 61/412,207, filed on Nov. 10, 2010.

(51) Int. Cl.
*C07D 333/34* (2006.01)
*A61K 31/18* (2006.01)

(52) U.S. Cl.
CPC .............. *C07D 333/34* (2013.01); *A61K 31/18* (2013.01)
USPC ........................................... 514/445; 549/65

(58) Field of Classification Search
USPC ............................................ 514/445; 549/65
See application file for complete search history.

(56) References Cited

U.S. PATENT DOCUMENTS

2001/0011135 A1    8/2001  Riedl et al.
2001/0021714 A1    9/2001  Chan et al.
(Continued)

FOREIGN PATENT DOCUMENTS

WO    01/49289 A1    7/2001

OTHER PUBLICATIONS

Lipson et al (Cell Metabolism 4, 245-254, Sep. 2006).*
Nakamura, et al., "Enantioselective Strecker-type reaction to sulfonylimines having a 2-pyridylsolfonyl group as a novel stereocontroller", Tetrahedron Letters 47 (2006) 7599-7602.
(Continued)

*Primary Examiner* — Savitha Rao
*Assistant Examiner* — Angela Brown-Pettigrew
(74) *Attorney, Agent, or Firm* — David J. Aston; Peters Verny, LLP

(57) ABSTRACT

The present invention directed to a method of treating multiple myeloma with the following compound:

or a pharmaceutically acceptable salt thereof. The compound is a novel small molecule inhibitor of Ire1.

1 Claim, 5 Drawing Sheets

(56) References Cited

U.S. PATENT DOCUMENTS

| | | |
|---|---|---|
| 2005/0026907 A1 | 2/2005 | Wash et al. |
| 2009/0227567 A1 | 9/2009 | Leftheris et al. |
| 2009/0291857 A1 | 11/2009 | Koong et al. |
| 2009/0312362 A1 | 12/2009 | Koong et al. |
| 2012/0202751 A1 | 8/2012 | Koong et al. |
| 2013/0150399 A1 | 6/2013 | Koong et al. |

OTHER PUBLICATIONS

International Search Report and Written Opinion, PCT/US2011/059821, dated Apr. 12, 2012.

Koong, et al., "Targeting XBP-1 as a Novel Anti-Cancer Strategy", Cancer Biology & Therapy, 5:7, 756-759, Jul. 2006.

Spiotto, et al., "Imaging the unfolded protein response in primary tumors reveals microenvironments with metabolic variations that predict tumor growth", Cancer Res 2010;70:78-88.

\* cited by examiner

IRE1ALPHA ENDONUCLEASE SPECIFIC INHIBITOR WITH CYTOTOXIC ACTIVITY

CROSS-REFERENCE TO RELATED APPLICATIONS

This application claims priority from U.S. Provisional Patent Application No. 61/412,207 filed on Nov. 10, 2010, which is hereby incorporated by reference in its entirety and is a U.S. national stage application of PCT/US2011/059821, which is also incorporated herein by reference in its entirety.

STATEMENT OF GOVERNMENTAL SUPPORT

This invention was made with government support under contract CA067166 awarded by the National Institutes of Health. The government has certain rights in this invention.

BACKGROUND OF THE INVENTION

1. Field of the Invention

The present invention relates to the field of anti-cancer therapy, and, more particularly to small molecule inhibitors of Ire 1 endonuclease activity.

2. Related Art

Presented below is background information on certain aspects of the present invention as they may relate to technical features referred to in the detailed description, but not necessarily described in detail. That is, individual parts or methods used in the present invention may be described in greater detail in the materials discussed below, which materials may provide further guidance to those skilled in the art for making or using certain aspects of the present invention as claimed. The discussion below should not be construed as an admission as to the relevance of the information to any claims herein or the prior art effect of the material described.

Multiple myeloma (MM) is a B cell neoplasm associated with unregulated/uncontrolled differentiation and proliferation of mature B cells to plasma cells. Despite significant therapeutic advances in recent years, MM remains an incurable disease in most patients (Raab M S, Podar K, Breitkreutz I, Richardson P G, Anderson K C. Multiple myeloma. Lancet. 2009; 374:324-339). Due to high production of secreted antibodies, MM cells display chronic ER stress, and their survival is dependent upon the adaptive Ire1-XBP1 branch of the unfolded protein response (UPR) pathway (Davenport E L, Moore H E, Dunlop A S, et al. Heat shock protein inhibition is associated with activation of the unfolded protein response pathway in myeloma plasma cells. Blood. 2007; 110(7): 2641-2649). Investigators have shown that perturbing the UPR with proteosome inhibitors can sensitize MM cells to apoptosis (Lee A H, Iwakoshi N N, Anderson K C, Glimcher L H. Proteasome inhibitors disrupt the unfolded protein response in myeloma cells. Proc Natl Acad Sci USA. 2003; 100:9946-9951). The FDA has approved the proteasome inhibitor bortezomib as the first example of a UPR modulating chemotherapy for the treatment of MM (Field-Smith A, Morgan G J, Davies F E. Bortezomib (Velcadetrade mark) in the Treatment of Multiple Myeloma. Ther Clin Risk Manag. 2006; 2:271-279).

Recent in vitro Ire1 kinase and RNase assays have yielded insight into determining the mechanism of Ire1 activation (Nock S, Gonzalez T N, Sidrauski C, Niwa M, Walter P. Purification and activity assays of the catalytic domains of the kinase/endoribonuclease Ire1p from *Saccharomyces cerevisiae*. Methods Enzymol. 2001; 342:3-10; Dong B H, Niwa M, Walter P, Silverman R H. Basis for regulated RNA cleavage by functional analysis of RNase L and Ire1p. Rna-a Publication of the Rna Society. 2001; 7:361-373). Mutant Ire1 proteins with amino acid substitutions at conserved positions in the kinase domain identified nucleotide binding and kinase-domain phosphorylation as necessary for Ire1 RNase activation (Tirasophon W, Welihinda A A, Kaufman R J. A stress response pathway from the endoplasmic reticulum to the nucleus requires a novel bifunctional protein kinase/endoribonuclease (Ire1p) in mammalian cells. Genes Dev. 1998; 12:1812-1824; Korennykh A V, Egea P F, Korostelev A A, et al. The unfolded protein response signals through high-order assembly of Ire1. Nature. 2009; 457:687-693; Han D, Lerner A G, Vande Walle L, et al. IRE1alpha kinase activation modes control alternate endoribonuclease outputs to determine divergent cell fates. Cell. 2009; 138:562-575). However, a report found that an ATP competitive inhibitor, 1NM-PP1, could activate Ire1 that contained a mutation in the ATP binding site. In this context, kinase activity was not required for Ire1 function, suggesting that Ire1 activity may be modulated through an allosteric mechanism (Papa F R, Zhang C, Shokat K, Walter P. Bypassing a kinase activity with an ATP-competitive drug. Science. 2003; 302:1533-1537.) The crystal structure of the cytosolic portion of activated yeast Ire1 revealed a back-to-back configuration of the kinase domain within the Ire1 dimer (Lee K, Dey M, Neculai D, Cao C, Dever T, Sicheri F. Structure of the dual enzyme Ire1 reveals the basis for catalysis and regulation in nonconventional RNA splicing. Cell. 2008; 132:89-100). This structure supported a model in which dimerization (or oligermization) of Ire1 juxtaposes kinase domains which facilitates trans-autophosphorylation of the protein, resulting in a competent nuclease pocket and enhanced Rnase activity (Korennykh A V, Egea P F, Korostelev A A, et al. The unfolded protein response signals through high-order assembly of Ire1. Nature. 2009; 457: 687-693; Han D, Lerner A G, Vande Waite L, et al. IRE1alpha kinase activation modes control alternate endoribonuclease outputs to determine divergent cell fates. Cell. 2009; 138: 562-575).

More recently, the flavanoid quercetin was shown to activate Ire1 through a newly described ligand-binding pocket along the Ire1 dimer interface (Wiseman R, Zhang Y, Lee K, et al. Flavonol activation defines an unanticipated ligand-binding site in the kinase-RNase domain of Ire1. Mol Cell. 2010; 38:291-304). These data suggest the pharmacologic potential for multiple ligands to selectively modulate either Ire1 kinase or RNase activity.

BRIEF SUMMARY OF THE INVENTION

The present invention concerns identification of an IRE1alpha endonuclease specific inhibitor with cytotoxic activity against human multiple myeloma We hypothesize that MM cells exist under inherent ER stress and that targeting the adaptive Ire1 -XBP1 response could be a promising therapeutic strategy. We report the identification of a novel class of compounds that specifically blocks the endonuclease activity of Ire1 without affecting its kinase activity. In support of our hypothesis, we show that a small molecule member of this class demonstrated significant single agent activity in MM xenograft and human MM ex-vivo studies.

The details of the invention are set forth in the accompanying description below. Although methods and materials similar or equivalent to those described herein can be used in the practice or testing of the present invention, illustrative methods and materials are now described. Other features, objects, and advantages of the invention will be apparent from the description and from the claims. In the specification and the appended claims, the singular forms also include the plural unless the context clearly dictates otherwise. Unless defined otherwise, all technical and scientific terms used herein have the same meaning as commonly understood by one of ordinary skill in the art to which this invention belongs.

BRIEF DESCRIPTION OF THE DRAWINGS

FIG. 2D shows tumor vol (mm3) vs. days for vehicle (top line) and STF.

FIG. 2E shows relative survival (%) vs. STF-083010 (µM) for MM cells; CD19+7AAD-; CD56+7AAD-; CD3+7ADD-cells (bottom line to top line at end points).

DETAILED DESCRIPTION OF THE PREFERRED EMBODIMENT

Overview

Provided herein are compounds of Formula I:

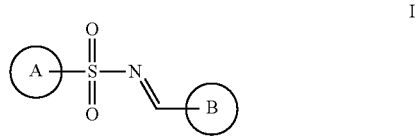

and pharmaceutically acceptable salts thereof,
wherein

A is an optionally substituted aryl or an optionally substituted heteroaryl group; and B is an optionally substituted aryl or an optionally substituted heteroaryl group;

provided that the compound is not (E)-N-((2-hydroxynaphthalen-1-yl)methylene)thiophene-2-sulfonamide.

In some embodiments, A is an optionally substituted heteroaryl group and B is an optionally substituted aryl group. In other embodiments, B is an optionally substituted bicyclic aryl group. In still other embodiments, the bicyclic aryl group is an optionally substituted napthalene group. In one embodiment, A is an optionally substituted thiophene.

Also provided are methods of treating a disease mediated by IRE1α, comprising administering to a patient in need thereof an effective amount of compound of Formula I':

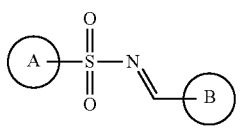

and pharmaceutically acceptable salts thereof,
wherein
A is an optionally substituted aryl or an optionally substituted heteroaryl group; and
B is an optionally substituted aryl or an optionally substituted heteroaryl group.

In some embodiments of the methods, A is an optionally substituted heteroaryl group and B is an optionally substituted aryl group. In other embodiments of the methods, B is an optionally substituted bicyclic aryl group. In still other embodiments of the methods, the bicyclic aryl group is an optionally substituted napthalene group. In one embodiment of the methods, A is an optionally substituted thiophene. In a particular embodiment of the methods, the compound is

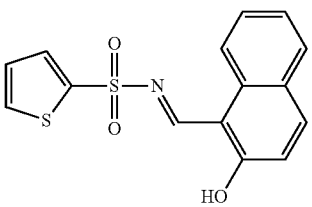 [SMILES: O=S(=O)(/N=C/c1c(O)ccc2ccccc12)c1cccs1]

or a pharmaceutically acceptable salt thereof.

In some embodiments, the disease is cancer. In one embodiment, the cancer is multiple myeloma.

Figure 1A:
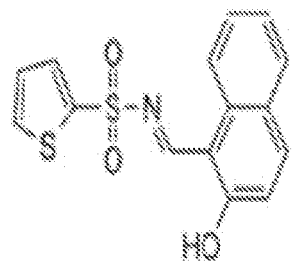
FIG. 1A is a drawing of the chemical structure of inhibitor STF-0803010.
Figure 1B:
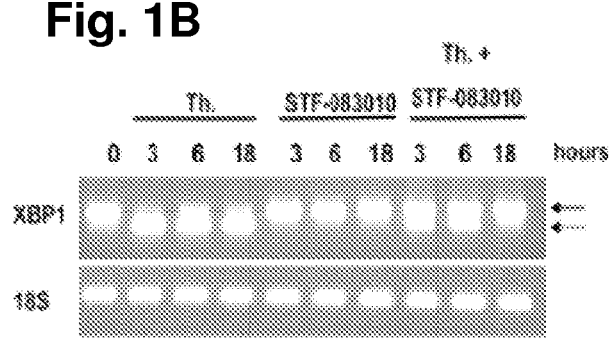
FIG. 1B is a gel electrophoresis image showing STF-083010 inhibiting endogenous XBP1 mRNA splicing. RPMI8226 cells were treated with 300 µM thapsigargin (Th), 60 µM STF-083010 or both for indicated amount of time and the relative XBP1 splicing was determined by RT-PCR. Solid arrow indicates the unspliced and broken arrow indicates the spliced form.
Figure 1C:
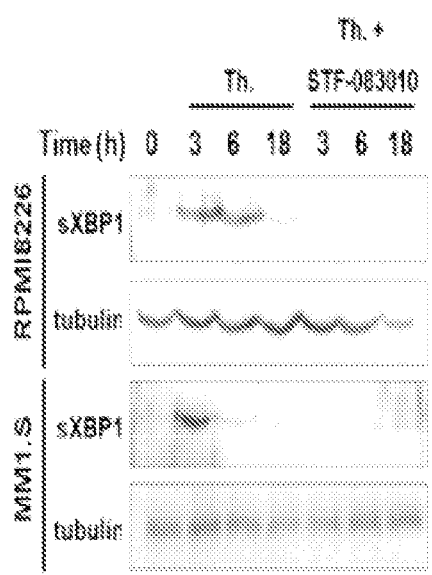
FIG. 1C is set of a gel electrophoresis images showing STF-083010 inhibiting the production of sXBP1 protein but not the auto-phosphorylation of Ire1α. The left panel indicates MM cell lines that were treated for the indicated times with 300 µM Th and 60 µM STF-083010 and sXBP1 protein was detected by immunoblotting. The right panel shows RPMI8226 cells that were treated with 300 µM Th and 60 µM STF-083010 for the indicated times and the levels of phosphorylated and total Ire1α were detected using specific antibodies.
Figure 1D:
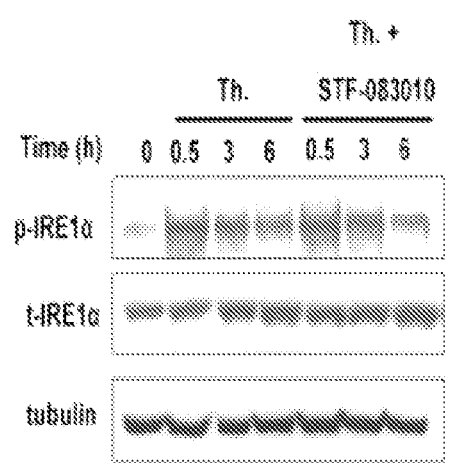
FIG. 1D is a set of gel electrophoresis images in which RPMI8226 cells were treated with 300 µM Th and 60 µM STF-083010 for the indicated times and the levels of phosphorylated and total Ire1α were detected using specific antibodies.
Figure 1E:
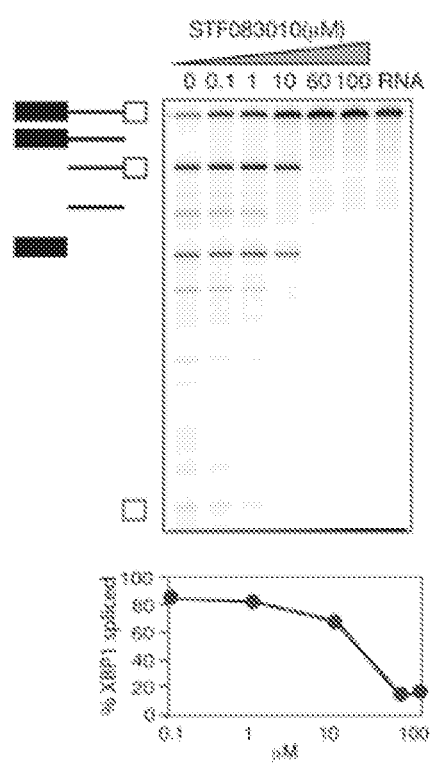
FIG. 1E is a gel electrophoresis image and a line graph showing the STF-083010 effect on cell free Ire1α RNase (endonuclease) activity. The gel electrophoresis image indicates that hIre1 was incubated with uniformly labeled (32P) HAC1 508 nt transcript for 30 min in the presence of increasing concentrations of STF-0830010 (1-100 µM). HAC1 mRNA cleavage reaction was analyzed by separation of products on denaturing polyacrylamide gels, followed by autoradiography. The line graph is the quantitation of HAC1 mRNA processing showing half-maximal inhibition at approximately 25 µM. Error bars represent s.e.m. of 3 independent experiments.
Figure 1F:
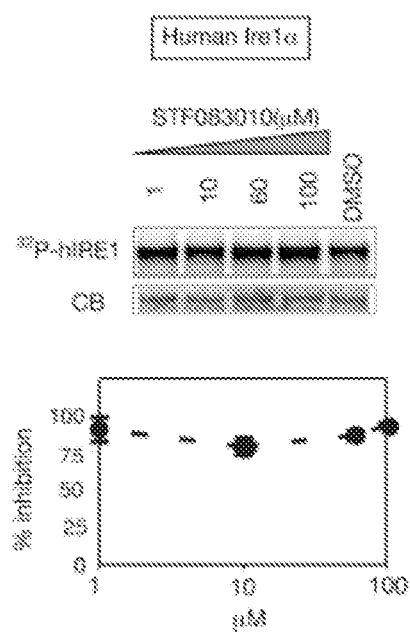
FIG. 1F is a graph and gel that show the effect of STF-083010 on cell free Ire1α kinase activity, Upper: hIre1α was incubated with 32P-γATP and increasing concentrations (0-100 µM) of STF-083010. Ire1α autophosphorylation was analyzed by SDS-PAGE, followed by autoradiography to determine the amount of 32P incorporation (32P-hIRE). Lower: kinase activity showed no significant change during co-incubation with STF-083010. Error bars represent s.e.m. of 3 independent experiments.

STF-083010 was identified in our cell-based reporter gene, high-throughput screen, and its structure is shown in FIG. 1A. To confirm the molecular target, we analyzed the effect of STF-083010 on endogenous XBP1 mRNA splicing levels in control and ER-stressed RPMI8226 human MM cells (FIG. 1B). Incubation with thapsigargin (Th), an inhibitor of ER calcium flux that induces ER stress, resulted in XBP1 splicing. However, with the addition of STF-083010, splicing was almost completely blocked. STF-083010 also inhibited XBP1 splicing activated by other types of ER stress, including tunicamycin treatment, glucose deprivation or severe hypoxia (data not shown). As expected, inhibiting XBP1 mRNA splicing also inhibited production of active sXBP1 protein (FIG. 1C). However, STF-083010 did not inhibit Ire1α kinase activity as shown in the immunoblot of auto-phosphorylated Ire1α (FIG. 1D). To establish that this effect was due to a direct interaction between STF-083010 and Ire1α, we analyzed Ire1α enzymatic activity in a cell free system. STF-083010 blocked Ire1α's endonuclease activity (FIG. 1E), without affecting its kinase activity (FIG. 1F).

Figure 2A:
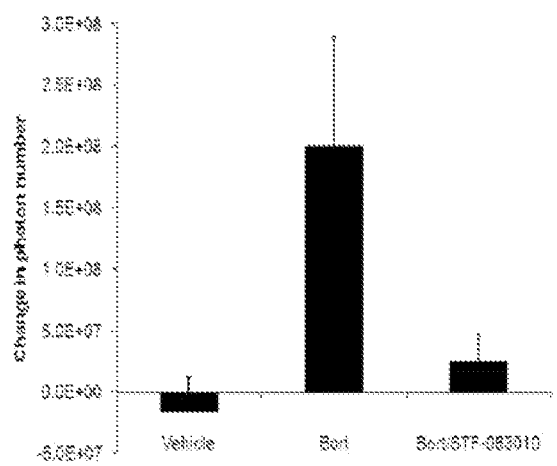
FIG. 2A is a bar graph showing that STF-083010 blocks bortezomib-induced XBP1 activity in vivo. Transgenic XBP1-luc mice were injected i.p. with drug vehicle (16% chremophor), 1 mg/kg bortezomib, or 1 mg/kg bortezomib and 60 mg/kg STF-083010 and bioluminescence was measured after 24 h. The graph shows the average change in the number of photons per animal 24 h after treatment. Error bars show s.e.m. of at least 4 animals.
Figure 2B:
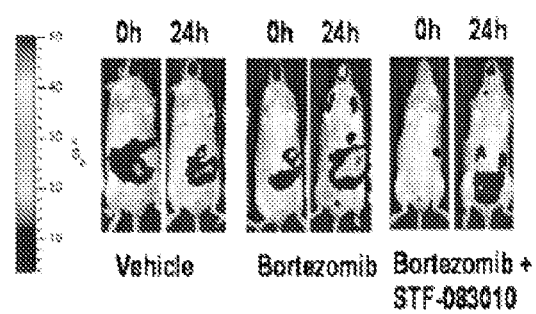
FIG. 2B is a set of images of representative mice before and after treatment.
Figure 3:
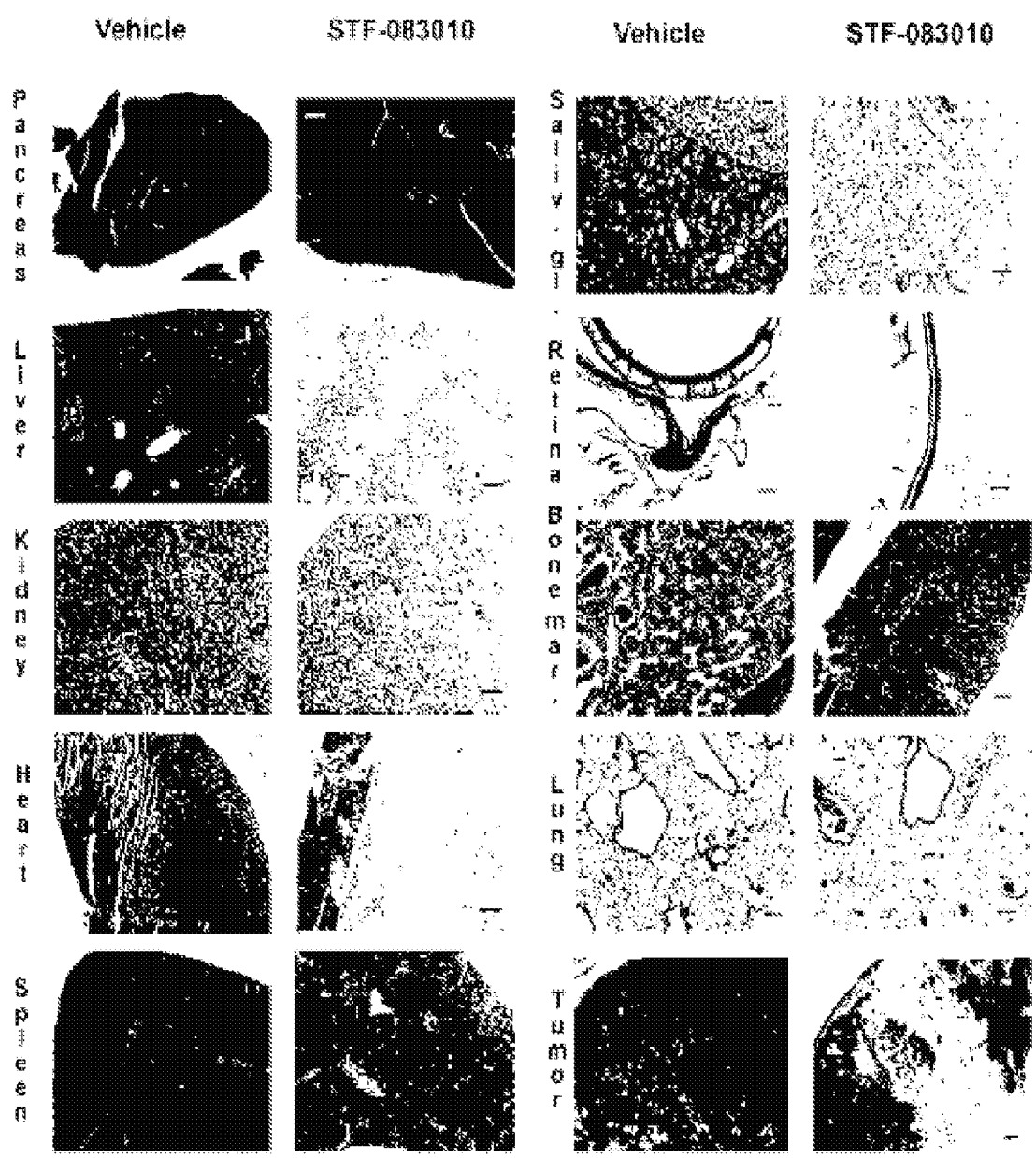
FIG. 3 is a set of images of the H&E stained sections of normal mouse tissues and RPMI8226 xenograft tumors treated with drug vehicle (16% chremophor in saline) or 30 mg/kg STF-083010 weekly for two weeks.

Next, we utilized transgenic mice harboring the same XBP1-luciferase reporter gene (Spiotto M T, Banh A, Papandreou I, et al. Imaging the unfolded protein response in primary tumors reveals microenvironments with metabolic variations that predict tumor growth. *Cancer Res.* 2010; 70:78-88) to determine the in vivo efficacy of STF-083010. Treatment of these reporter mice with bortezomib induced ER stress and a commensurate increase in XBP1-luciferase bioluminescent activity. However, when STF-083010 was injected with bortezomib, there was no increase in bioluminescent signal (FIGS. 2A, 2B). This inhibition was not due to cellular toxicity in the animals, as we did not find any histologic effects of STF-083010 after treatment at doses used in these studies (60 mg/kg×1 and 30 mg/kg×2) (FIG. 3).

Figure 2C:
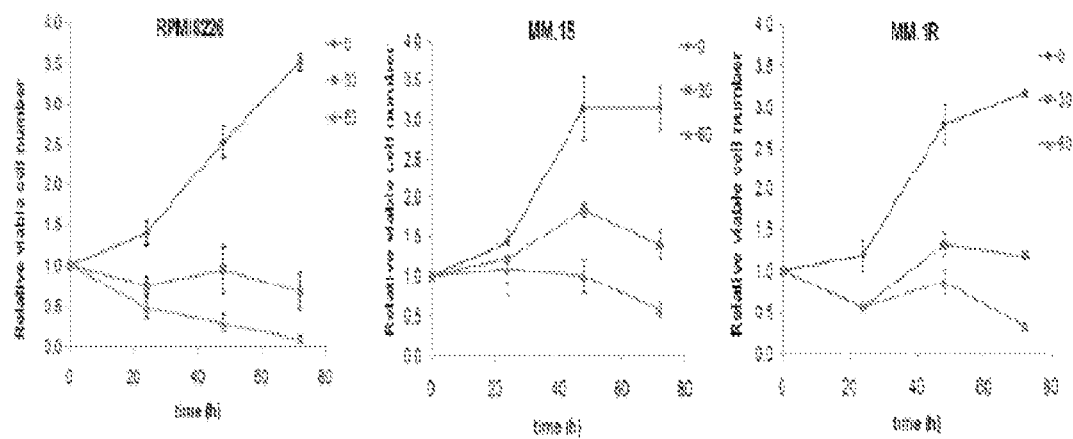
FIG. 2C is a set of line graphs showing in vitro cytotoxicity of STF-083010. RPMI8226, MM.1S and MM.1R MM cells that were treated with 0, 30 or 60 µM of STF-083010 and viable cell number was measured daily by the trypan blue exclusion method.
Figure 2D:
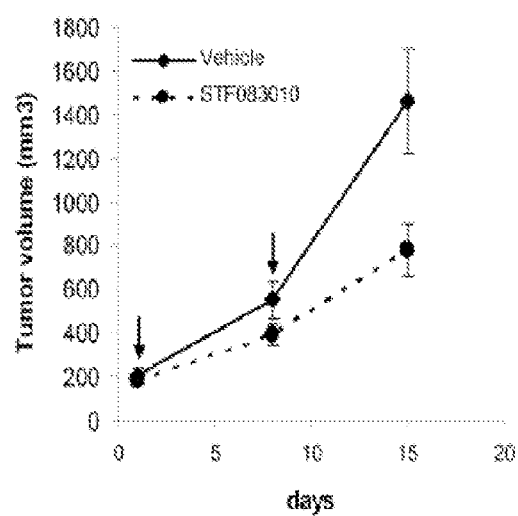
FIG. 2D is a line graph showing the antitumor activity of STF-083010 in vivo. RPMI8226 MM cells were established as subcutaneous tumor xenografts in NOD/SCID/IL2Rγ null mice. When tumors reached an average volume of 150 mm3, 2 groups of 5 mice each were treated with 30 mg/kg STF-083010 or drug vehicle once weekly for 2 weeks.
Figure 2E:
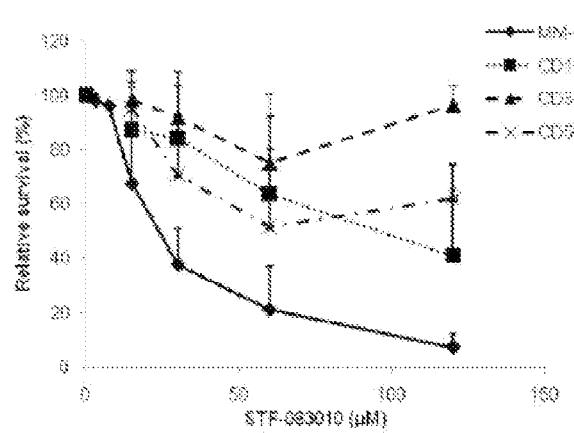
FIG. 2E is a line graph showing that STF-083010 is preferentially cytotoxic against human MM cells. MM cells were obtained by CD138+ selection from bone marrow samples from MM patients; lymphocytes were obtained by Ficoll density-gradient centrifugation of peripheral blood samples from control patients, followed by staining with anti CD3, anti CD19 and anti CD56 monoclonal antibodies to differentiate between T-, B- and NK cells. Cells were cultured with the indicated concentrations of STF-083010 for 24 h and cell viability was measured by flow cytometric analysis of Annexin V/Propidium Iodide (MM) or 7-aminoactinomycin D (peripheral blood lymphocytes) stained samples.

In order to determine anti-myeloma activity of STF-083010, first we treated a panel of MM cell lines with increasing concentrations of the compound in vitro and measured viability by trypan blue exclusion (FIG. 2C). STF-083010 showed cytostatic and cytotoxic activity in a dose- and time-dependent manner. Next, we treated RPMI8226 human MM cells grown as tumor xenografts in NSG mice. Intraperitoneal injection of STF-083010 alone (d1, d8) significantly inhibited the growth of these tumors (FIG. 2D). Additionally, we treated fresh CD138+ cells isolated from MM patients and compared the ex vivo toxicity to that of cells from 7 control patients (FIG. 2E, Tables 1,2). STF-083010 was selectively cytotoxic to CD 138+ cells compared to B (CD19+), T (CD3+), and NK (CD56+) cells.

TABLE 1

Patient characteristics and LD50 (24 h) of STF-083010 in multiple myeloma cells.

| UPN | Sex (M/F) | Age (years) | Type | Cytogenetics | Previous Treatments | Bortezomib Resistance | LD50 (uM) 24 h |
|---|---|---|---|---|---|---|---|
| 1 | M | 75 | Aκ | Del 13 | 6 | N | 37.0 |
| 2 | M | 72 | Gλ | NI | 6 | Y | 23.1 |
| 3 | F | 75 | Gκ | NI | 0 | N | 19.2 |
| 4 | M | 50 | LCκ | Del 13 | 1 | N | 36.5 |
| 5 | F | 68 | Gκ | NI | 7 | Y | 22.3 |
| 6 | M | 72 | Aκ | NI | 0 | N | 09.0 |
| 7 | M | 75 | Gκ | NI | 0 | N | 26.4 |
| 8 | M | 77 | Aκ | NI | 3 | N | 48.7 |
| AVERAGE | | | | | | | 27.8 |

TABLE 2

LD50 (24 h) of STF-083010 in T-, B- and NK cells.

| | | | | LD50 (uM) | | |
|---|---|---|---|---|---|---|
| UPN | Sex (M/F) | Age (years) | Condition | CD3 positive | CD19 positive | CD56 positive |
| 9 | M | 59 | MM | 97.2 | 40.7 | 62.0 |
| 10 | F | 73 | MM | 129.4 | 45.0 | 29.5 |
| 11 | M | 79 | MM | 59.5 | 70.3 | 41.6 |
| 12 | F | 22 | PNH | 64.2 | 26.5 | 42.0 |
| 13 | F | 31 | Leucopenia | 246.1 | 89.5 | 121.0 |
| 14 | F | 80 | CML | 270.4 | 165.3 | 133.6 |
| 15 | F | 58 | AML | 89.5 | 74.1 | 69.5 |
| AVERAGE | | | | 136.6 | 73.1 | 71.3 |

Compounds of the present invention can be synthesized using synthetic chemistry techniques available to those of skill in the art as described in, for example, "March's Advanced Organic Chemistry: Reactions, Mechanisms, and Structure," 6th Edition, Wiley, 2007 (ISBN: 978-0-471-72091-1).

In summary, we have identified a novel class of compounds with the unique property that specifically blocks the endonuclease activity of Ire1 without affecting its kinase function. These small molecules represent a new class of targeted agents with significant anti-cancer activity in various in vitro and in vivo models of MM.

EXAMPLES

The disclosure is further illustrated by the following examples, which are not to be construed as limiting this disclosure in scope or spirit to the specific procedures herein described. It is to be understood that the examples are provided to illustrate certain embodiments and that no limitation to the scope of the disclosure is intended thereby. It is to be further understood that resort may be had to various other embodiments, modifications, and equivalents thereof which may suggest themselves to those skilled in the art without departing from the spirit of the present disclosure and/or scope of the appended claims.

Chemical library screening. The screen was performed in the Stanford High-Throughput Bioscience Center (HTBC). hIre1α protein containing both Ire1 cytoplasmic kinase and RNase domains was expressed and purified from baculovirus as described (Niwa M, Sidrauski C, Kaufman R J, Walter P. A role for presenilin-1 in nuclear accumulation of Ire1 fragments and induction of the mammalian unfolded protein response. *Cell.* 1999; 99:691-702). Autophosphorylation activity was determined with the addition of $^{32}$P-γATP. Endonuclease activity was determined with the addition of radiolabeled HAC1 508 nt RNA substrate synthesized in vitro using $α^{32}$P-UTP (Nock S, Gonzalez T, Sidrauski C, Niwa M, Walter P. Purification and activity assays of the catalytic domains of the kinase/endoribonuclease Ire1p from *Saccharomyces cerevisiae. Methods Enzymol.* 2001; 342:3-10). STF083010 was incubated with recombinant hIRE1α protein, radio-labeled HAC1 508 nt RNA, and appropriate buffers. Kinase activity and RNAse cleavage products were quantitated by PAGE and $^{32}$P-γATP or $^{32}$P-UTP autoradiography respectively.

Human specimen isolation and assays. Bone marrow aspirates were obtained from MM patients after obtaining informed consent according to institutional guidelines. CD138+ plasma cells were selected by positive magnetic bead selection (StemCell Technologies, Vancouver, Canada) either after isolation of nucleated cells (patients 1-4) or directly (patients 5-8). Peripheral blood cells were obtained by Ficoll-Hypaque density centrifugation from separate control patients. Cell culture, reporter assays, RT-PCR, Western blotting, and bioluminescent imaging. Standard assay conditions were used as previously described (Spiotto M T, Banh A, Papandreou I, et al. Imaging the unfolded protein response in primary tumors reveals microenvironments with metabolic variations that predict tumor growth. *Cancer Res.* 2010; 70:78-88; Romero-Ramirez L, Cao H, Nelson D, et al. XBP1 is essential for survival under hypoxic conditions and is required for tumor growth. *Cancer Res.* 2004; 64:5943-5947).

CONCLUSION

The above specific description is meant to exemplify and illustrate the invention and should not be seen as limiting the scope of the invention, which is defined by the literal and equivalent scope of the appended claims. Any patents or publications mentioned in this specification are intended to convey details of methods and materials useful in carrying out certain aspects of the invention which may not be explicitly set out but which would be understood by workers in the field. Such patents or publications are hereby incorporated by reference to the same extent as if each was specifically and individually incorporated by reference and contained herein, as needed for the purpose of describing and enabling the method or material referred to.

EQUIVALENTS

Those skilled in the art will recognize, or be able to ascertain, using no more than routine experimentation, numerous equivalents to the specific embodiments described specifically herein. Such equivalents are intended to be encompassed in the scope of the following claims.

What is claimed is:
1. A method of treating multiple myeloma comprising administering to a patient in need thereof an effective amount of the compound below:

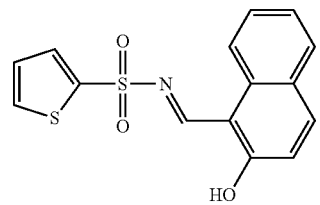 [SMILES: O=S(=O)(/N=C/c1c(O)ccc2ccccc12)c1cccs1]

or a pharmaceutically acceptable salt thereof.

* * * * *